US007223870B2

(12) United States Patent
Ghosh et al.

(10) Patent No.: US 7,223,870 B2
(45) Date of Patent: May 29, 2007

(54) METHODS FOR PREPARING N-ARYLATED OXAZOLIDINONES VIA A COPPER CATALYZED CROSS COUPLING REACTION

(75) Inventors: Arun Ghosh, Madison, CT (US); Stephane Caron, Stonington, CT (US); Janice E. Sieser, Ivoryton, CT (US)

(73) Assignee: Pfizer Inc., New York, NY (US)

( * ) Notice: Subject to any disclaimer, the term of this patent is extended or adjusted under 35 U.S.C. 154(b) by 431 days.

(21) Appl. No.: 10/645,779

(22) Filed: Aug. 21, 2003

(65) Prior Publication Data

US 2004/0122226 A1 Jun. 24, 2004

Related U.S. Application Data

(60) Provisional application No. 60/423,328, filed on Nov. 1, 2002.

(51) Int. Cl.
 *C07D 263/04* (2006.01)
(52) U.S. Cl. ..................... 548/229; 548/230
(58) Field of Classification Search ............... 544/137; 546/123, 252, 209; 548/229, 230
See application file for complete search history.

(56) References Cited

U.S. PATENT DOCUMENTS 6,307,087 B1  10/2001  Buchwald et al. .......... 558/388
6,313,142 B1  11/2001  Damon et al. .............. 514/313

FOREIGN PATENT DOCUMENTS

WO    WO 2085838    10/2002

OTHER PUBLICATIONS

Kang, S. K., et al., Copper-catalyzed N-arylation of Aryl Iodides with Benzamides or Nitrogen Heterocycles in the Presence of Ethylenediamine, *Synlett*, No. 3, pp. 427-430, (2002).
Mallesham, B., et al., Highly Efficient CuI-Catylyzed Coupling of Aryl Bromides with Oxazolidnones Using Buchwald's Protocol: A Short Route to Linezolid and Toloxatone, *Organic Letters*, vol. 5, No. 7, pp. 963-965, (2003).
Chan, D. M. T., Promotion of Reaction of N-H Bonds with Triarylbismuth and Cupric Acetate, *Tetrahedron Letters*, vol. 37, No. 50, pp. 9013-9016, (1996).
Chan, D. M. T., et al., New N- and O-Arylations with Phenylboronic Acids and Cupric Acetate, *Tetrahedron Letters*, vol. 39, pp. 2933-2936 (1998).
Antilla J. C. et al., Journal of the American Chemical Society, vol. 124, pp. 11684-11688, 2002, "The Copper-Catalyzed N-Arylation of Indoles."
Madar D. J. et al., Tetrahedron Letters, vol. 42, pp. 3681-3684, 2001, "Synthesis of N-arylated oxazolidinones via a palladium catalyzed cross coupling reaction. Application to the synthesis of the antibacterial agent Dup-721."
Cacchi S. et al., American Chemical Society, Organic Letters, vol. 3, No. 16, pp. 2539-2541, 2001, "3-Aryl-2-oxazolidinones through the Palladium-Catalyzed N-Arylation of 2-Oxazolidinones."

*Primary Examiner*—Johann Richter
*Assistant Examiner*—Ebenezer Sackey
(74) *Attorney, Agent, or Firm*—Gregg C. Benson; Lisa A. Samuels

(57) ABSTRACT

Methods for the preparation of N-arylated oxazolidinone compounds via a copper catalyzed cross coupling reaction are disclosed.

2 Claims, No Drawings

METHODS FOR PREPARING N-ARYLATED OXAZOLIDINONES VIA A COPPER CATALYZED CROSS COUPLING REACTION

CROSS REFERENCE TO RELATED APPLICATION

This application claims the benefit of U.S. Provisional Application No. 60/423,328 filed Nov. 1, 2002.

FIELD OF THE INVENTION

This invention relates to intermediates useful in the preparation of CETP inhibitors and methods of preparation thereof.

BACKGROUND OF THE INVENTION

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S.

Risk for development of this condition has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D. J., et al.: "High-density Lipoprotein Cholesterol and Cardiovascular Disease", Circulation, (1989), 79: 8–15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high-density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues resulting in reduced compliance. Fibrates and the HMG-CoA reductase inhibitors raise HDL-C only modestly. As a result, there is a significant unmet medical need for a well-tolerated agent, which can significantly elevate plasma HDL levels, thereby reversing or slowing the progression of atherosclerosis.

PCT application publication number WO 00/02887 discloses the use of catalysts comprising certain novel ligands for transition metals in transition metal-catalyzed carbon-heteroatom and carbon-carbon bond formation.

Commonly assigned U.S. Pat. No. 6,140,343, the disclosure of which is incorporated herein by reference, discloses, inter alia, the CETP inhibitor, cis-4-[acetyl-(3,5-bis-trifluoromethyl-benzyl)-amino]-2-ethyl-6-trifluoromethyl-3,4-dihydro-2H-quinoline-1-carboxylic acid isopropyl ester, and processes for the preparation thereof.

Commonly assigned U.S. Pat. No. 6,197,786, the disclosure of which is incorporated herein by reference, discloses, inter alia, the CETP inhibitor, cis-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, and processes for the preparation thereof.

SUMMARY

According to one aspect of the present invention there is provided a method for preparing a compound of formula I

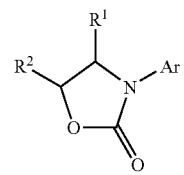

wherein $R^1$ is a partially saturated, fully saturated or fully unsaturated $(C_1-C_4)$ straight or branched carbon chain wherein the carbons, other than the connecting carbon, may optionally be replaced with one heteroatom selected independently from oxygen, sulfur and nitrogen wherein said carbon atoms are optionally mono-, di- or tri-substituted independently with halo, said carbon is optionally mono-substituted with oxo or hydroxy, said sulfur is optionally mono- or di-substituted with oxo, said nitrogen is optionally mono- or di-substituted with oxo; or said $R^1$ is a partially saturated, fully saturated or fully unsaturated three to five membered ring optionally having one heteroatom selected independently from oxygen, sulfur and nitrogen; wherein said $R^1$ ring is optionally mono-, di- or tri-substituted independently with halo, $(C_1-C_6)$alkoxy, nitro, $(C_1-C_4)$alkyloxycarbonyl;

$R^2$ is hydrogen, $C_1-C_4$ alkyl, $C_3-C_6$ cycloalkyl, $C_2-C_6$ alkenyl, $C_2-C_6$ alkynyl, $C_1-C_4$ alkoxy, $C_1-C_4$ alkoxy-$C_1-C_4$ alkyl;

phenyl optionally substituted with $C_1-C_6$ alkoxy or OY wherein Y is a hydroxy protecting group, halogen, $C_1-C_4$ alkyl, $C_2-C_6$ alkenyl, $C_2-C_6$ alkynyl, $C_1-C_4$ alkoxy, $C_1-C_4$ alkoxy-$C_1-C_4$ alkyl, trifluoromethyl, nitro, carbo-$C_1-C_4$ alkoxy, $C_1-C_4$ alkoxy carbonyl, carbonyl, or cyano;

or benzyl with the phenyl moiety of the benzyl optionally substituted with $C_1-C_6$ alkoxy or OY wherein Y is a hydroxy protecting group, halogen, $C_1-C_4$ alkyl, $C_2-C_6$ alkenyl, $C_2-C_6$ alkynyl, $C_1-C_4$ alkoxy-$C_1-C_4$ alkyl, trifluoromethyl, amido, nirto, carbo-$C_1-C_4$ alkoxy, $C_1-C_4$ alkoxy-carbonyl, carbonyl or cyano;

Ar is aromatic moiety as described below comprising reacting a compound of formula II

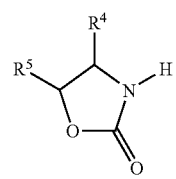

wherein $R^4$ is a partially saturated, fully saturated or fully unsaturated $(C_1-C_4)$ straight or branched carbon chain wherein the carbons, other than the connecting carbon, may optionally be replaced with one heteroatom selected independently from oxygen, sulfur and nitrogen wherein said carbon atoms are optionally mono-, di- or tri-substituted independently with halo, said carbon is optionally mono-substituted with oxo or hydroxy, said sulfur is optionally mono- or di-substituted with oxo, said nitrogen is optionally mono- or di-substituted with oxo; or said $R^1$ is a partially saturated, fully saturated or fully unsaturated three to five membered ring optionally having one heteroatom selected independently from oxygen, sulfur and nitrogen; wherein said $R^1$ ring is optionally mono-, di- or tri-substituted independently with halo, $(C_1–C_6)$alkoxy, nitro, $(C_1–C_4)$alkyloxycarbonyl;

$R^5$ is hydrogen, $C_1–C_4$ alkyl, $C_3–C_6$ cycloalkyl, $C_2–C_6$ alkenyl, $C_2–C_6$ alkynyl, $C_1–C_4$ alkoxy, $C_1–C_4$ alkoxy-$C_1–C_4$ alkyl;

phenyl optionally substituted with $C_1–C_6$ alkoxy or OY wherein Y is a hydroxy protecting group, halogen, $C_1–C_4$ alkyl, $C_2–C_6$ alkenyl, $C_2–C_6$ alkynyl, $C_1–C_4$ alkoxy, $C_1–C_4$ alkoxy-$C_1–C_4$ alkyl, trifluoromethyl, nitro, carbo-$C_1–C_4$ alkoxy, $C_1–C_4$ alkoxy-carbonyl, carbonyl, or cyano;

or benzyl with the phenyl moiety of the benzyl optionally substituted with $C_1–C_6$ alkoxy or OY wherein Y is a hydroxy protecting group, halogen, $C_1–C_4$ alkyl, $C_2–C_6$ alkenyl, $C_2–C_6$ alkynyl, $C_1–C_4$ alkoxy-$C_1–C_4$ alkyl, trifluoromethyl, amido, nirto, carbo-$C_1–C_4$ alkoxy, $C_1–C_4$ alkoxy-carbonyl, carbonyl or cyano;

with an aryl halide of formula III

Ar-L    (III)

wherein Ar is Ar is an aromatic hydrocarbon or heteroaromatic moiety selected from the group consisting of phenyl, naphthyl, pyridyl, thiophenyl, furanyl, pyrrolyl and pyrimidyl, imidazolyl, oxazolyl, thiazolyl, triazolyl, pyrazolyl, pyrazinyl, pyridazinyl each of which may be optionally substituted by one or more, preferably one to two, substituents independently selected from the group consisting of halogen, $C_1–C_4$ alkyl, $C_2–C_6$ alkenyl, $C_2–C_6$ alkynyl, $C_1–C_4$ alkoxy, $C_1–C_4$ alkoxy-$C_1–C_4$ alkyl, trifluoromethyl ($CF_3$), nirto, carbo-$C_1–C_4$ alkoxy, $C_1–C_4$ alkoxy-carbonyl, carbonyls (ketones and aldehydes), cyano;

L is an activated leaving group, such as a halide, preferably iodide or bromide; or alkyl- or aryl-sulfonate, such as mesylate, triflate, tosylate in the presence of a bidentate ligand of formula IV

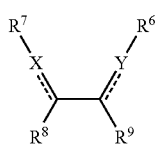

(IV)

wherein $R^6$, $R^7$, $R^8$, $R^9$ are independently selected from hydrogen, cyclic or acyclic $C_1–C_6$ alkyl, alkenyl, aryl, X and Y are independently selected from nitrogen and oxygen; where nitrogen is incorporated as an amine or imine or as a part of nitrogen heterocylce; where oxygen is incorporated as a hydroxy, alkoxy, or oxo substituent, and in the presence of a copper catalyst.

According to another aspect of the present invention there is provided a method for preparing the compound of formula I as described above wherein the activated leaving group is an iodide or bromide.

According to another aspect of the present invention there is provided a method for preparing the compound of formula I as described above wherein the ligand is N,N-dimethyl ethylenediamine.

According to another aspect of the present invention there is provided a method for preparing the compound of formula I as described above wherein the ligand is 1,2-diaminocyclohexane.

Still another aspect of the present invention provides a compound (R)-4-ethyl-3-(4-trifluoromethyl-phenyl)-oxazolidin-2-one of formula V

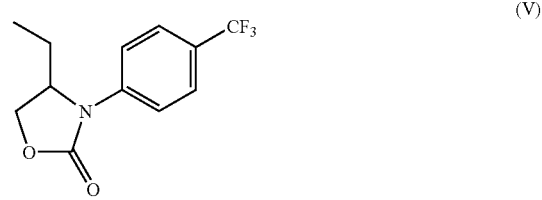

(V)

Another aspect of the present invention provides a compound (R)-4-ethyl-3-(4-trifluoromethyl-phenyl)-[1,2,3]oxathiazolidine 2-oxide of formula V

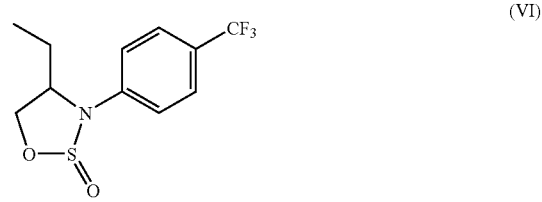

(VI)

Liqands Used in the N-arylation Sequence:

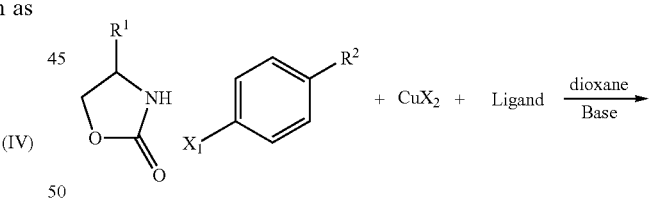

+ $CuX_2$ + Ligand $\xrightarrow{\text{dioxane}}{\text{Base}}$

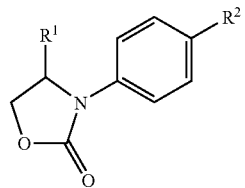

LIGANDS:

A= 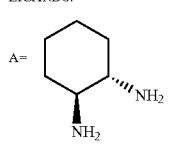   B= 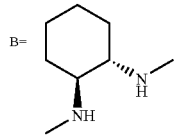

-continued

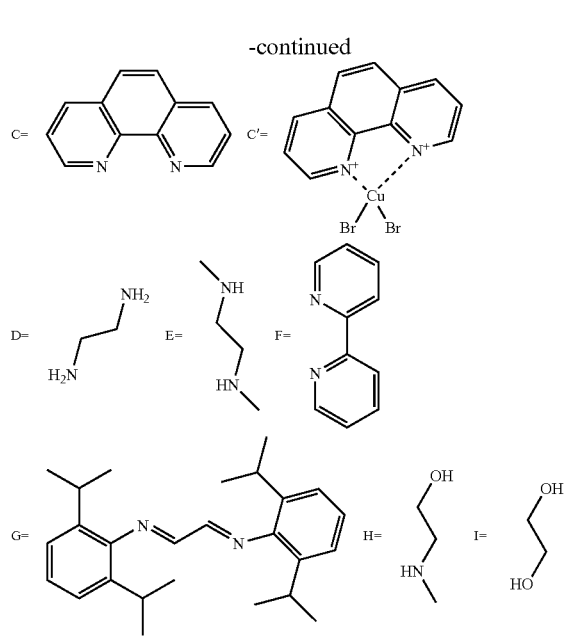

TABLE

Conditions for N-arylation

| $R_1$ (%) | $R_2$ | $X_1$ | $X_2$ | BASE | HR | LIGAND | YIELD |
|---|---|---|---|---|---|---|---|
| Ph | C(O)NHC$_3$H$_7$ | Br | I | K$_2$CO$_3$ | 18 | A | 93 |
| Ph | CN | Br | I | K$_2$CO$_3$ | 23 | A | 95 |
| Ph | H | Br | I | K$_2$CO$_3$ | 23 | A | 95 |
| Ph | H | I | I | K$_2$CO$_3$ | 20 | A | 66 |
| Ph | H | I | I | K$_3$PO$_4$ | 18 | E | 93 |
| Ph[1] | H | I | I | K$_3$PO$_4$ | 18 | E | 38 |
| Ph | CF$_3$ | I | I | K$_3$PO$_4$ | 18 | E | 98 |
| Ph | F | I | I | K$_3$PO$_4$ | 18 | E | 85 |
| Ph[1] | F | I | I | K$_3$PO$_4$ | 18 | E | 45 |
| Ph | CF$_3$ | Br | — | K$_2$CO$_3$ | 16 | C' | 70 |
| Ph | CF$_3$ | Br | — | K$_2$CO$_3$ | 22 | C' | 80 |
| Ph | CF$_3$ | Br | I(3%) | K$_2$CO$_3$ | 16 | C' | 41 |
| Ph | CF$_3$ | Br | Br$_2$ | K$_2$CO$_3$ | 16 | C | 41 |
| Ph | CF$_3$ | Br | Br$_2{}^2$ | K$_2$CO$_3$ | 16 | C | 55 |
| Ph | CF$_3$ | Br | Br$_2{}^2$ | K$_2$CO$_3$ | 16 | A | 90 |
| Ph | CF$_3$ | Br | Br$_2{}^2$ | K$_2$CO$_3$ | 17 | F | 6 |
| Ph | CF$_3$ | Br | Br$_2{}^2$ | K$_2$CO$_3$ | 17 | D | 33 |
| Ph | CF$_3$ | Br | Br$_2{}^2$ | K$_2$CO$_3$ | 22 | B | 12 |
| Ph | CF$_3$ | Br | Br$_2{}^2$ | K$_2$CO$_3$ | 22 | E | 95 |
| Et | CF$_3$ | Br | I | K$_2$CO$_3$ | 19 | A | 85 |
| Et | CF$_3$ | Br | Br$_2{}^2$ | K$_2$CO$_3$ | 16 | A | 95 |
| Et | CF$_3$ | Br | Br$_2{}^2$ | K$_2$CO$_3$ | 16 | E | 66 |
| Et | CF$_3$ | Br | Br$_2{}^2$ | K$_2$CO$_3$ | 16 | H | 25 |
| Et | CF$_3$ | Br | Br$_2{}^2$ | K$_2$CO$_3$ | 16 | I | 12 |

Typical Conditions: (mMol) oxazolidinone:aryl halide:Cu:Ligand:Base: dioxane 1:1:0.1:0.1:2:1 ml
[1]Toluene substituted for dioxane In this specification and in the claims that follow, reference will be made to a number of terms that shall be defined to have the following meanings:

"Alkyl" refers to the radical of saturated aliphatic groups, including straight-chain alkyl groups, branched-chain alkylgroups cycloalkyl (alicyclic) groups, alkyl substituted cycloalkyl groups, and cycloalkyl substituted alkyl groups. Moreover, the term "alkyl is intended to include both "unsubstituted alkyls" and "substituted alkyls", the latter of which refers to alkyl moieties having substituent replacing a hydrogen on one or more carbons of the hydrocarbon backbone. Such substituent can include, for example, a halogen, a hydroxyl, a carbonyl (such as carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulthydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieies substituted on the hydrocarbon chain can themselves be substituted, if appropriate.

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituent as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g. the other cyclic rings can be cycloalkyls, cycloalkenyls, cycloalkynyls, aryls and/or heterocyclyls.

The term "heteroatom" as used herein means an atom of any element other than carbon or hydrogen. Preferred heteroatoms are nitrogen, oxygen, sulfur and phosphorous.

The terms "amine" and "amino" are art recognized and refer to both unsubstituted and substituted amines.

The terms "alkoxyl" or "alkoxy" refer to an alkyl group, as defined above, having an oxygen radical attached thereto.

The terms "imine" or "imido" refer to a nitrogen-containing organic substance having a carbon to nitrogen double bond.

The term "halide" refers to fluoride, chloride, bromide and iodide.

The term "halogen" refers to fluorine, chlorine, bromine, iodine and astatine.

The term "hydroxyl" indicates the OH$^-$ group in an organic compound.

Chemical structures herein are represented by planar chemical structure diagrams that are viewed from a perspective above the plane of the structure. A wedge line (?)appearing in such chemical structures represents a bond that projects up from the plane of the structure.

DETAILED DESCRIPTION OF THE INVENTION

In general, the oxazolidinone, aryl halide, copper catalyst, and base are charged in a flask under nitrogen atmosphere. The flask is evacuated and backfilled with $N_2$ before adding the solvent (preferably ethereal) and a bidentate, chelating-ligand. The reaction mixture is then heated to the desired temperature until the starting materials are consumed, as judged by LCMS. The reaction mixture is then cooled, diluted, and filtered. The combined filtrates are concentrated and dried to produce the desired oxazolidinones.

The general nature of this copper-catalyzed N-arylation of oxazolidinones was established using copper having a formal oxidation state of (0), (I) or (II) or a combination thereof as a catalyst, and is sometimes referred herein as "copper catalyst". Inorganic salts of copper that may be used include the iodide, bromide, and chloride with copper (I) iodide being preferred. In addition to the prescribed solvent in the typical procedure, several other polar solvents, e.g., DMF, NMP, toluene, DME, and bases, including carbonates, phosphates, hydroxide, or alkoxide, preferably carbonates, are useful for this transformation.

The aryl halide and the oxazolidinone substrates may be used in an ideal molar ratio of about 1:1, or to completely consume one of the components, e.g., aryl halide or oxazolidinone, either reagent may be used in excess. A suitable molar ratio of aryl halide or oxazolidinone to base is in the range of from about 1:1 to 1:5. A more preferred molar ratio of aryl halide or oxazolidinone to base is in the range of from about 1:1 to 1:3.

Normally, the molar ratio of the copper catalyst to substrate aryl halide or oxazolidinone is in the range of from about 0.15:1 to about 0.05:1; a preferred molar ratio of the copper catalyst to substrate aryl halide or oxazolidinone is about 0.1:1. The molar ratio copper catalyst to the ligand is in the range of from about 1:0.5 to about 1:5; preferably in the range of from 1:1 to about 1:2.

The order of addition of the various components to the reaction vessel does not affect the outcome of the reaction. Thus, solid components may be conveniently added to the vessel together, prior to the addition of the liquid components as a solution in appropriate solvent. Once all the components are present in the same reaction vessel, the mixture may be heated to the desired reaction temperature.

Reaction Scheme A illustrates the preferred process for preparing the chiral isomer of formula I via a copper catalyzed coupling of 1-bromo-4-trifluoromethyl-benzene and (R)-4-ethyl-oxazolidin-2-one.

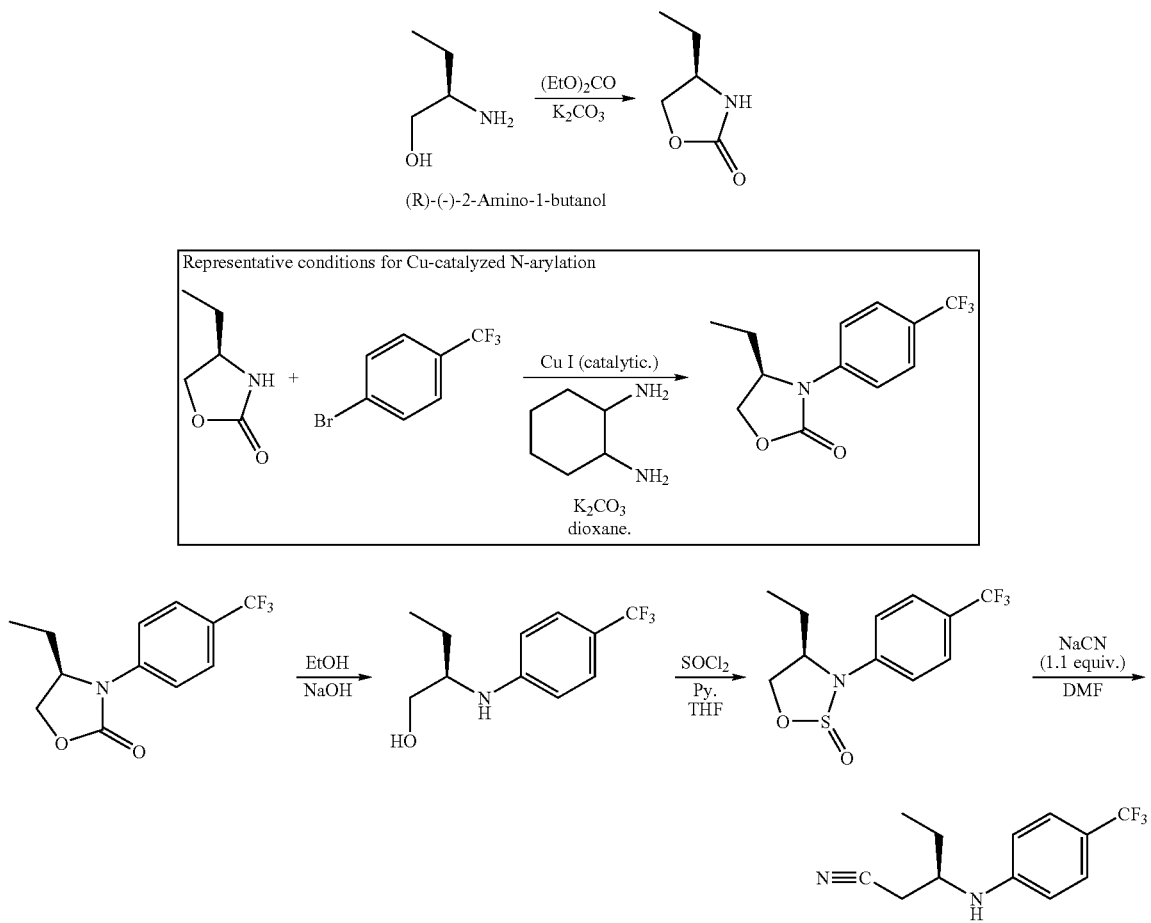

Scheme A
Copper-catalyzed approach to (R)-3-(4-trifluoromethyl-phenylamino)-pentanenitrile General Procedure All commercially available reagents were used as received without further purification. Solvents were purged with nitrogen prior to use. Flash chromatography was performed on silica gel 60 (230–400 mesh). All reactions were monitored by TLC, and/or, LC-MS. $^1$H and $^{13}$C nuclear magnetic resonance (NMR) spectra were recorded on a 400 MHz NMR spectrometer (Varian, Incorporated) at ambient temperature in CDCl₃ (Cambridge Isotope Laboratories, Incorporated) unless otherwise stated.

According to Scheme A, the formula II compound (R)-3-(4-trifluoromethyl-phenylamino)-pentanenitrile was prepared as follows:

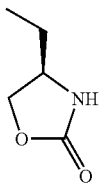

(R)-4-ethyl-oxazolidin-2-one.

(R)-2-amino-1-butanol (42 mL/0.44 mol), diethylcarbonate (107 mL/0.89 mol) and potassium carbonate (6.12 g/0.044 mol) were heated in an oil bath set between 135°–140°. A distillate was collected at approximately 90° (79 mL). Heating was continued until distillation ceased.

After cooling to room temperature, the reaction mixture was diluted with 40 mL CH₂Cl₂ and washed with water (3×), and brine. Drying (over MgSO₄), concentration and vacuum drying gave the oxazolidinone as a pale yellow oil (39.75 g) in 78% yield.

¹H NMR (400 MHz, CDCl₃) δ 0.9 (t, J=7.5 Hz, 3 H) 1.6 (m, 2 H), 3.8 (m, 1 H), 4.0 (dd, J=8.5, 6.0 Hz, 1 H), 4.5 (t, J=8.5 Hz,1 H), 6.8 (s, 1 H).

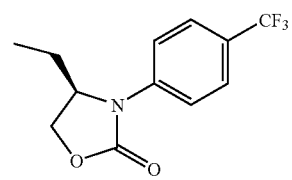

(R)-4-ethyl-3-(4-trifluoromethyl-phenyl)-oxazolidin-2-one

K₂CO₃ (12.0 g/87 mMol) and CuI (0.83 g/4.4 mMol) were charged to a flask under N₂. 4-ethyl-oxazolidin-2-one (5.0 g/43.5 mMol) and 1-bromo-4-trifluoromethyl-benzene (6.0 mL/42.8 mMol) each diluted in 20 mL dioxane added to the flask followed by 1,2-diaminocyclohexane (0.52 mL/4.4 mMol). The bright blue mixture was heated to 1100 and held for 22 hours.

The cooled mixture was diluted with CH₂Cl₂ and filtered through celite. The filtrate was concentrated to an amber oil and purified by silica chromatography to give the product in 86% yield.

Mass Spec 260.2 (m+1).

¹H NMR (400 MHz, CDCl₃) δ 0.91 (t, J=7.5, 3H), 1.63–1.82 (m, 2H), 4.17–4.21 (m, 1H), 4.44–4.45 (m, 1H), 4.53–4.58 (m, 1H), 7.59–7.65 (m,4H).

¹³C NMR (CDCl₃) δ 7.89, 24.44, 56.67, 66.56, 120.7, 126.52, 140.25, 155.60.

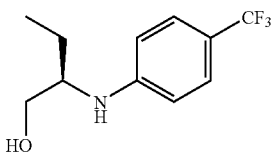

(R)-2-(4-trifluoromethyl-phenylamino)-butan-1-ol

NaOH (9.25 mL of 12.5 N/115 mMol) diluted in 10 mL water was added to a solution of 4-ethyl-3-(4-trifluoromethyl-phenyl)-oxazolidin-2-one (5.99 g/23.11 mMol) in 10 mL EtOH. The mixture was heated to 500 and held for 30 minutes. HPLC/MS indicated the reaction was complete. The cooled mixture was concentrated and diluted with MTBE. The pH was adjusted to 6 with dilute HCl and the layers separated. The aqueous layer was extracted twice more with MTBE and the combined extracts washed with brine, dried, (Na₂SO₄), and concentrated to give 5.2 g of the aminol as an amber oil (yield 97%).

¹H NMR (400 MHz, CDCl₃) ? 1.0 (t, J=7.5 Hz, 3 H), 1.6 (dd, J=14.5, 7.1 Hz, 1 H), 1.6 (m, 1 H), 3.4 (m, 1 H), 3.6 (m, 1 H), 3.7 (dd, J=10.8, 4.1 Hz, 1 H), 6.6 (d, J=8.3 Hz, 2 H), 7.4 (d, J=8.7 Hz, 2 H).

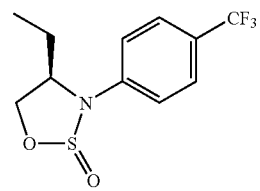

(R)-4-ethyl-3-(4-trifluoromethyl-phenyl)-[1,2,3]oxathiazolidine 2-oxide

SOCl₂ (0.66 mL/9 mMol) and pyridine (3.5 mL/43 mMol) were stirred together in 13.5 mL ice cold anhydrous THF under N₂. 2-(4-trifluoromethyl-phenylamino)-butan-1-ol (1.0 g/4.3 mMol) dissolved in 45 mL anhydrous THF added dropwise over 40 minutes to the rapidly stirred mixture. HPLC indicated no starting material remained after the addition. Water (20 mL) was slowly added to the cold mixture and the mixture extracted twice with MTBE. The combined extracts were washed with water (3×) and brine, dried (MgSO₄) and concentrated to a yellow oil. After vacuum drying the oxathiozolidine was recovered as a waxy solid in 81% yield (0.974 g).

¹H NMR (400 MHz, CDCl₃) δ 1.0 (t, J=7.5 Hz, 3 H), 1.6 (m, 1 H), 1.7 (m, 1 H), 4.5 (dd, J=8.7, 2.5 Hz, 1 H), 4.9 (m, 1 H), 5.1 (dd, J=8.9, 6.0 Hz, 1 H), 7.1 (d, J=8.3 Hz, 2 H), 7.6 (m, 2 H). ¹³C NMR (100 MHz, CDCl₃) δ 9.7, 23.9, 58.2, 74.0, 117.1, 118.4, 127.2, 142.4.

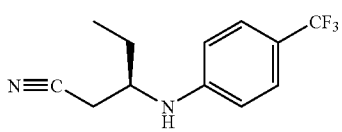

(R)-3-(4-trifluoromethyl-phenylamino)-pentanenitrile

NaCN (0.38 g/7.8 mMol) was added to room temperature solution of 4-ethyl-3-(4-trifluoromethyl-phenyl)-[1,2,3]oxathiazolidine 2-oxide (0.85 g/3.1 mMol) in 10 mL anhydrous DMF. The mixture was heated to 50° for 12 hours. MTBE and water were added to the cooled mixture and the layers separated. The aqueous layer was extracted twice more with MTBE and the combined extracts washed with 1 N HCl and brine. The desired nitrile was isolated as a yellow oil in 81% yield (0.6 g) after drying over MgSO$_4$ and concentration. Both chiral HPLC and H$^1$ NMR of the product were identical to a known standard of CP-696,775, cyclopropanemethanol, methanesulfonate.

$^1$H NMR (400 MHz, CDCl$_3$) δ 1.1 (t, J=7.5 Hz 3 H), 1.8 (m, 2 H), 2.6 (d, J=4.1 Hz, 1 H), 2.7 (m, 1 H), 3.7 (m, 1 H), 6.6 (d, J=8.3 Hz 2 H), 7.4 (d, J=8.7 Hz, 2 H).

The following Examples illustrate the preparation of N-aryl oxazolidinones of the present invention. The Examples are not intended to be limiting to the scope of the invention in any respect, and should not be so construed.

EXAMPLES 1–6

Example 1

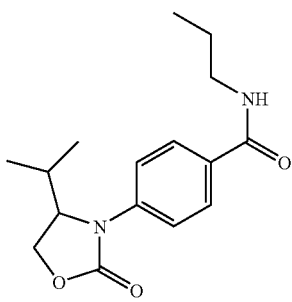

(S)-4-(4-Isopropyl-2-oxo-oxazolidin-3-yl)-N-propyl-benzamide

K$_2$CO$_3$ (0.272 g/2 mMol) and CuI (0.019 g/0.1 mMol) were charged to a flask under N$_2$. (S)-4-isopropyl-oxazolidin-2-one (0.155 g/1.2 mMol) and 1-bromo-4-N-propyl-benzamide(0.242 g/1 mMol) each diluted in 1 mL dioxane added to the flask followed by 1,2-diaminocyclohexane (0.012 mL/0.1 mMol). The bright blue mixture was heated to 110° and held for 22 hours.

The cooled mixture was diluted with CH$_2$Cl$_2$ and filtered through celite. The filtrate was concentrated to an amber oil and purified by silica chromatography to give the product in 75% yield.

Mass spec: 291.4 (m+1).

$^1$H NMR (CDCl$_3$) δ 0.77 (d, J=6.8, 3H), 0.88 (d, J=7.0, 3H), 0.91–0.95 (m, 3H), 1.57–1.63 (m, 2H), 2.07–2.15 (m, 1H), 3.33–3.38 (m, 2H), 4.20–4.24 (m,1H), 4.37–4.41 (m,1H), 4.43–4.46 (m,1H), 6.72–6.75 (m,1H), 7.48 (d, J=8.7, 2H), 7.77 (d, J=8.7, 2H).

$^{13}$C NMR (CDCl$_3$) δ 11.86, 14.34, 17.81, 23.05, 27.67, 42.02, 60.25, 62.78, 121.18, 128.28, 131.34, 139.55, 155.95, 167.07.

Example 2

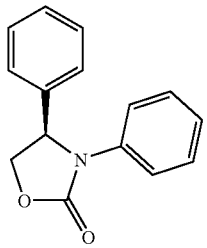

(R)-3,4-Diphenyl-oxazolidin-2-one

The procedure described in example 1 was used with the appropriate substitution of reagents as follows:

K$_2$CO$_3$ (0.275 g/2 mMol), CuI (0.019 g/0.1 mMol), (R)-4-phenyl-oxazolidin-2-one (0.163 g/1 mMol), Bromobenzene (0.1 ml/1 mMol), 1,2-diaminocyclohexane (0.012 mL/0.1 mMol) and 1 mL dioxane. The product was recovered in 99% yield.

Mass Spec 240.3 (m+1).

$^1$H NMR (CDCl$_3$) δ 4.21 (dd, J=5.81, 6.22, 1H), 4.78 (t, J=8.71, 1H), 5.40 (dd, J=6.22, 6.22, 1H), 7.06 (t, J=7.47, 1H), 7.24–7.40 (m, 9H).

$^{13}$C NMR (CDCl$_3$) δ 60.90, 70.07, 121.06, 124.91, 126.48, 129.14, 129.60, 137.23, 138.46, 156.19.

Example 3

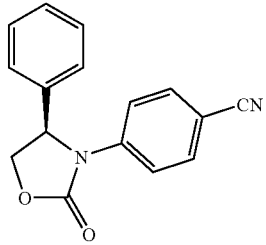

(R)-4-(2-Oxo-4-phenyl-oxazolidin-3-yl)-benzonitrile

The procedure described in example 1 was used with the appropriate substitution of reagents as follows:

K$_2$CO$_3$ (0.276 g/2 mMol), CuI (0.019 g/0.1 mMol), (R)-4-phenyl-oxazolidin-2-one (0.195 g/1.2 mMol), 4-Bromobenzonitrile (0.182 g/1 mMol), 1,2-diaminocyclohexane (0.012 mL/0.1 mMol) and 1 mL dioxane. The product was recovered in 82% yield.

Mass Spec 265.2 (m+1).

$^1$H NMR (CDCl$_3$) δ 4.17 (dd, J=5.6, 8.7, 1H), 4.78 (t, J=8.7, 1H), 5.46 (dd, J=5.6, 8.7, 1H), 7.24–7.37 (m, 5H), 7.44 (d, J=8.9, 2H), 7.55 (d, J=8.7, 2H)

$^{13}$C NMR (CDCl$_3$) δ 60.19, 70.20, 107.31, 118.89, 120.18, 126.2, 129.42, 129.90, 133.17, 137.64, 141.40, 155.48.

Example 4

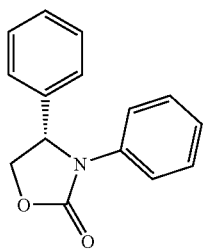

(S)-3,4-Diphenyl-oxazolidin-2-one

The procedure described in example 1 was used with the appropriate substitution of reagents as follows:

$K_2CO_3$ (0.553 g/4 mMol), CuI (0.039 g/0.2 mMol), (S)-4-phenyl-oxazolidin-2-one (0.325 g/2 mMol), Iodobenzene (0.22 ml/2 mMol), 1,2-diaminocyclohexane (0.024 mL/0.2 mMol) and 2 mL dioxane. The product was recovered in 66% yield.

Example 5

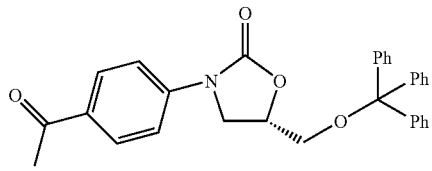

(S)-3-(4-Acetyl-phenyl)-5-trityloxymethyl-oxazolidin-2-one

The procedure described in example 1 was used with the appropriate substitution of reagents as follows:

$K_2CO_3$ (0.276 g/2 mMol), CuI (0.019 g/0.1 mMol), (S)-5-trityloxymethyl-oxazolidin-2-one (0.359 g/1 mMol), 4'-Bromoacetophenone (0.201 g/1 mMol), N,N'-Dimethylethylenediamine (0.01 mL/0.1 mMol) and 1 mL dioxane. The product was recovered in 92% yield.

Mass Spec 478.2 (m+1).

1H NMR (400 MHz, CHLOROFORM-D) δ ppm) 2.60 (s, 3H) 3.26 (dd, J=10.4, 3.7 Hz, 1 H) 3.55–3.59 (m, 1 H) 3.8 (dd, J=8.7, 5.4 Hz, 1 H) 4.05–4.10 (m, 1 H) 4.72–4.78 (m, 1 H) 7.21–7.29 (m, 9 H) 7.38–7.45 (m, 6 H) 7.66–7.68 (m, 2 H) 7.99–8.01 (m, 2 H).

Example 6

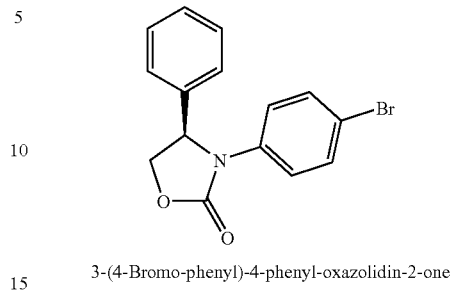

3-(4-Bromo-phenyl)-4-phenyl-oxazolidin-2-one

The procedure described in example 1 was used with the appropriate substitution of reagents as follows:

$K_2CO_3$ (0.276 g/2 mMol), CuI (0.022 g/0.11 mMol), oxazol (0.161 g/0.99 mMol), 4'-Bromobromobenzene (0.236 g/1.0 mMol), 1,2-diaminocyclohexane (0.1 ml/0.1 mMol). The product was recovered in 45% yield after chromatography.

Mass spec 318.1 (m+1).

$^1$H NMR (CDCl$_3$) δ 4.19 (dd, J=6.01, 6.01, 1H), 4.78 (t, J=8.8, 1H), 5.36 (dd, J=6.01, 6.01, 1H), 7.26–7.38 (m, 9H).

$^{13}$C NMR (CDCl$_3$) δ 60.70, 70.04, 117.84, 122.40, 126.42, 129.27, 129.75, 132.13, 136.36, 137.94, 155.90.

The invention claimed is:

1. A method for preparing a compound of formula I

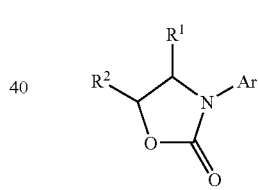

wherein $R^1$ is a partially saturated, fully saturated or fully unsaturated $(C_1–C_4)$ straight or branched carbon chain wherein the carbons, other than the connecting carbon, may optionally be replaced with one heteroatom selected independently from oxygen, sulfur and nitrogen wherein said carbon atoms are optionally mono-, di- or tri-substituted independently with halo, said carbon is optionally mono-substituted with oxo or hydroxy, said sulfur is optionally mono- or di-substituted with oxo, said nitrogen is optionally mono- or di-substituted with oxo; or said $R^1$ is a partially saturated, fully saturated or fully unsaturated three to five membered ring optionally having one heteroatom selected independently from oxygen, sulfur and nitrogen; wherein said $R^1$ ring is optionally mono-, di- or tri-substituted independently with halo, $(C_1–C_6)$alkoxy, nitro, $(C_1–C_4)$alkyloxycarbonyl;

$R^2$ is hydrogen, $C_1$–$C_4$ alkyl, $C_3$–$C_6$ cycloalkyl, $C_2$–$C_6$ alkenyl, $C_2$–$C_6$ alkynyl, $C_1$–$C_4$ alkoxy, $C_1$–$C_4$ alkoxy-$C_1$–$C_4$ alkyl;

phenyl optionally substituted with $C_1$–$C_6$ alkoxy or OY wherein Y is a hydroxy protecting group, halogen, $C_1$–$C_4$ alkyl, $C_2$–$C_6$ alkenyl, $C_2$–$C_6$ alkynyl, $C_1$–$C_4$ alkoxy, $C_1$–$C_4$ alkoxy-$C_1$–$C_4$ alkyl, trifluoromethyl, nitro, carbo-$C_1$–$C_4$ alkoxy, $C_1$–$C_4$ alkoxy-carbonyl, carbonyl, or cyano;

or benzyl with the phenyl moiety of the benzyl optionally substituted with $C_1$–$C_6$ alkoxy or OY wherein Y is a hydroxy protecting group, halogen, $C_1$–$C_4$ alkyl, $C_2$–$C_6$ alkenyl, $C_2$–$C_6$ alkynyl, $C_1$–$C_4$ alkoxy-$C_1$–$C_4$ alkyl, trifluoromethyl, amido, nirto, carbo-$C_1$–$C_4$ alkoxy, $C_1$–$C_4$ alkoxy-carbonyl, carbonyl or cyano;

wherein is Ar is an aromatic hydrocarbon or heteroaromatic moiety selected from the group consisting of phenyl, naphthyl, pyridyl, thiophenyl, furanyl, pyrrolyl and pyrimidyl, imidazolyl, oxazolyl, thiazolyl, triazolyl, pyrazolyl, pyrazinyl, pyridazinyl each of which may be optionally substituted by one or more, preferably one to two, substituents independently selected from the group consisting of halogen, hydroxyl, $C_1$–$C_4$ alkyl, $C_2$–$C_6$ alkenyl, $C_2$–$C_6$ alkynyl, $C_1$–$C_4$ alkoxy, $C_1$–$C_4$ alkoxy-$C_1$–$C_4$ alkyl, trifluoromethyl ($CF_3$), amino, amido, imines, nirto, carbo-$C_1$–$C_4$ alkoxy, $C_1$–$C_4$ alkoxy-carbonyl, carbonyls (ketones and aldehydes), cyano;

comprising reacting a compound of formula II

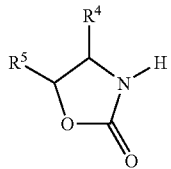

(II)

wherein $R^4$ is a partially saturated, fully saturated or fully unsaturated ($C_1$–$C_4$) straight or branched carbon chain wherein the carbons, other than the connecting carbon, may optionally be replaced with one heteroatom selected independently from oxygen, sulfur and nitrogen wherein said carbon atoms are optionally mono-, di- or tri-substituted independently with halo, said carbon is optionally mono-substituted with oxo or hydroxy, said sulfur is optionally mono- or di-substituted with oxo, said nitrogen is optionally mono- or di-substituted with oxo; or said $R^1$ is a partially saturated, fully saturated or fully unsaturated three to five membered ring optionally having one heteroatom selected independently from oxygen, sulfur and nitrogen; wherein said $R^1$ ring is optionally mono-, di- or tri-substituted independently with halo, ($C_1$–$C_6$)alkoxy, nitro, ($C_1$–$C_4$)alkyloxycarbonyl;

$R^5$ is hydrogen, $C_1$–$C_4$ alkyl, $C_3$–$C_6$ cycloalkyl, $C_2$–$C_6$ alkenyl, $C_2$–$C_6$ alkynyl, $C_1$–$C_4$ alkoxy, $C_1$–$C_4$ alkoxy-$C_1$–$C_4$ alkyl;

phenyl optionally substituted with $C_1$–$C_6$ alkoxy or OY wherein Y is a hydroxy protecting group, halogen, $C_1$–$C_4$ alkyl, $C_2$–$C_6$ alkenyl, $C_2$–$C_6$ alkynyl, $C_1$–$C_4$ alkoxy, $C_1$–$C_4$ alkoxy-$C_1$–$C_4$ alkyl, trifluoromethyl, nitro, carbo-$C_1$–$C_4$ alkoxy, $C_1$–$C_4$ alkoxy-carbonyl, carbonyl, or cyano;

or benzyl with the phenyl moiety of the benzyl optionally substituted with $C_1$–$C_6$ alkoxy or OY wherein Y is a hydroxy protecting group, halogen, $C_1$–$C_4$ alkyl, $C_2$–$C_6$ alkenyl, $C_2$–$C_6$ alkynyl, $C_1$–$C_4$ alkoxy-$C_1$–$C_4$ alkyl, trifluoromethyl, amido, nirto, carbo-$C_1$–$C_4$ alkoxy, $C_1$–$C_4$ alkoxy-carbonyl, carbonyl or cyano;

with an aryl halide of formula III

Ar-L     (III)

wherein Ar is an aromatic hydrocarbon or heteroaromatic moiety selected from the group consisting of phenyl, naphthyl, pyridyl, thiophenyl, furanyl, pyrrolyl and pyrimidyl, imidazolyl, oxazolyl, thiazolyl, triazolyl, pyrazolyl, pyrazinyl, and pyridazinyl each of which may be optionally substituted by one or more, preferably one to two, substituents independently selected from the group consisting of halogen, $C_1$–$C_4$ alkyl, $C_2$–$C_6$ alkenyl, $C_2$–$C_6$ alkynyl, $C_1$–$C_4$ alkoxy, $C_1$–$C_4$ alkoxy-$C_1$–$C_4$ alkyl, trifluoromethyl ($CF_3$), nirto, carbo-$C_1$–$C_4$ alkoxy, $C_1$–$C_4$ alkoxy-carbonyl, carbonyls (ketones and aldehydes), cyano;

L is an activated leaving group, such as a halide, preferably iodide or bromide; or alkyl- or aryl-sulfonate, such as mesylate, triflate, tosylate in the presence of N,N-dimethyl ethylenediamine and in the presence of a copper catalyst.

2. The method according to claim 1 wherein the activated leaving group is an iodide or bromide.

* * * * *